(12) United States Patent
Shakur et al.

(10) Patent No.: US 11,013,470 B2
(45) Date of Patent: May 25, 2021

(54) DETECTING ABNORMALITIES IN ECG SIGNALS

(71) Applicant: Cambridge Heartwear Limited, Cambridge (GB)

(72) Inventors: Rameen Shakur, Cambridge (GB); James Charles, Cambridge (GB); Roberto Cipolla, Cambridge (GB)

(73) Assignee: Cambridge Heartwear Limited, Cambridge (GB)

( * ) Notice: Subject to any disclaimer, the term of this patent is extended or adjusted under 35 U.S.C. 154(b) by 181 days.

(21) Appl. No.: 16/003,844

(22) Filed: Jun. 8, 2018

(65) Prior Publication Data

US 2019/0374166 A1    Dec. 12, 2019

(51) Int. Cl.
| | | |
|---|---|---|
| A61B 5/04 | (2006.01) | |
| A61B 5/00 | (2006.01) | |
| G06K 9/62 | (2006.01) | |
| A61B 5/327 | (2021.01) | |
| A61B 5/332 | (2021.01) | |
| A61B 5/361 | (2021.01) | |
| A61B 5/366 | (2021.01) | |

(52) U.S. Cl.
CPC .......... *A61B 5/7267* (2013.01); *A61B 5/0006* (2013.01); *A61B 5/0022* (2013.01); *A61B 5/327* (2021.01); *A61B 5/332* (2021.01); *A61B 5/361* (2021.01); *A61B 5/366* (2021.01); *A61B 5/7221* (2013.01); *G06K 9/6223* (2013.01)

(58) Field of Classification Search
CPC ... A61B 5/7267; A61B 5/7264; A61B 5/0006; A61B 5/0456; A61B 5/0452; A61B 5/361; A61B 5/327; A61B 5/332; A61B 5/0022; A61B 5/7221; G06K 9/6223
See application file for complete search history.

(56) References Cited

U.S. PATENT DOCUMENTS

| | | | | |
|---|---|---|---|---|
| 2016/0232340 | A1* | 8/2016 | Feng | G06K 9/6249 |
| 2019/0099162 | A1* | 4/2019 | Keshet | A61B 8/463 |

OTHER PUBLICATIONS

NHS, "Arrhythmia", Jul. 8, 2015, London, UK, downloaded Sep. 6, 2018, http://www.nhs.uk/conditions/arrhythmia/Pages/arrhythrnia.aspx.

Atrial Fibrillation Assoc., Warwickshire, Anticoagulation Europe; "The AF report. Atrial fibrillation—preventing a stroke crisis", Kent, UK, Apr. 12, 2012, http://www.preventaf-strokecrisis.org/files/files/The AF Report 14 April 2012.pdf.

(Continued)

*Primary Examiner* — Mallika D Fairchild
(74) *Attorney, Agent, or Firm* — Patterson Thuente Pedersen, P.A.

(57) ABSTRACT

A method of detecting abnormalities in an ECG signals, comprising receiving an ECG signal, extracting at least one ECG beat the ECG signal; providing the at least one ECG beat to a neural network. Within the neural network, performing at least two layers of convolution operations, and for a beat of the ECG signal, determining a confidence map for the location of each of the P, Q, R, S and T points, determining, from the respective confidence maps the position or absence of points, the points comprising each of the P, Q, R, S and T points; and reporting the positions and/or absence of the points.

5 Claims, 5 Drawing Sheets

(56) References Cited

OTHER PUBLICATIONS

K. Carroll, S. Murad, J. Eliahoo, A. Majeed, "Stroke incidence and risk factors in a population-based prospective cohort study," Office for National Statistics, Newport, South Wales, UK, Rep. Health Statistics Quarterly 12, 2001. http://www.ons.gov.uk/ons/rel/hsq/health-statistics-quarterly/no-12-winter-2001/stroke-incidence-and-risk-factors-in-a-population-based-prospective-cohort-study.pdf.

C. Marini et al., Abstract of "Contribution of atrial fibrillation to incidence and outcome of ischemic stroke: results from a population-based study," Stroke, vol. 36, pp. 1115-1119, May 5, 2005.

D. M. Lloyd-Jones et al., Abstract of "Lifetime risk for development of atrial fibrillation: the Framingham heart study," Circulation, vol. 110, No. 9, pp. 1042-1046, Aug. 31, 2004.

G. Y. H. Lip and H. S. Lim, Abstract of "Atrial fibrillation and stroke prevention," The Lancet Neurology, vol. 6, No. 11, pp. 981-993, Nov. 2007.

M. Cesarelli, P. Bifulco, and M. Bracale, "An algorithm for the detection of the atrial fibrillation from the surface ECG for an of home-care evaluation of the implanted atrial defibrillators," in Proc. Mediterranean Conf. Medical and Biological Eng. and Computing, Cyprus, 1998, 5 pgs.

M. Carrara et al., Abstract of "Classification of cardiac rhythm using heart rate dynamical measures: validation in MIT-BIH databases," J. of Electrocardiology, vol. 48, No. 6, pp. 943-946, Nov.-Dec. 2015.

J. S. Healy et al., "Subclinical atrial fibrillation and the risk of stroke," The New England J. of Medicine, vol. 366, No. 2, pp. 120-129, Jan. 12, 2012.

Melo, SL, Caloba, LP, and Nadal, J. Arrhythmia analysis using artificial neural network and decimated electrocardiographic data, Computers in Cardiology 2000, pp. 73-76.

Moody, George B and Mark, Roger G. "A new method for detecting atrial fibrillation using RR intervals", Computers in Cardiology, 10(1):227-230, 1983.

Pan, Jiapu and Tompkins, Willis J. "A real-time QRS detection algorithm", IEEE transactions on biomedical engineering, (3):230-236, 1985.

Clifford, GD, Liu, CY, Moody, B, Lehman, L, Silva, I, Li, Q, Johnson, AEW, and Mark, RG. "AF classification from a short single lead ecg recording: The physionet/computing in cardiology challenge 2017", 2017.

Artis, Shane G, Mark, RG, and Moody, GB. "Detection of atrial fibrillation using artificial neural networks". In Computers in Cardiology 1991, Proceedings., pp. 173-176. IEEE, 1991.

Levin Tan. Fourth year project technical report regarding Atrial Fibrillation, date unknown, 44 pgs.

Schwab, P., Scebba, G., Zhang, J., Delai, M. and Karlen, W. "Beat by Beat: Classifying Cardiac Arrhythmias with Recurrent Neural Networks", Mobile Health Systems Lab, Department of Health Sciences and Technology ETH Zurich, Switzerland, Oct. 24, 2017, 4 pgs.

Rajpurkar, P., Hannun, A.Y., Haghpanahi, M., Bourn, C. and NG, A.Y. "Cardiologist-level arrhythmia detection with convolutional neural networks", Jul. 6, 2017, 9 pgs.

Pfister, T. and Charles, J. and Zisserman, A. "Flowing ConvNets for Human Pose Estimation in Videos, International Conference on Computer Vision", 2015, 9 pgs.

Yu, F. and Koltun, V. "Multi-scale context aggregation by dilated convolutions", Published as a conference paper at ICLR, Apr. 30, 2016, 13 pgs.

* cited by examiner

DETECTING ABNORMALITIES IN ECG SIGNALS

FIELD OF THE INVENTION

The present disclosure relates to a method and apparatus for detecting abnormalities in electrocardiogram (ECG) signal, and to a system for improving cardiovascular health.

BACKGROUND TO THE INVENTION

Every year, more than 2 million people in the UK are affected by cardiac arrhythmia (heart rhythm abnormalities) which can lead to stroke, cardiac arrest, or even sudden cardiac death. In particular, atrial fibrillation (AF) is responsible for 20% of all strokes caused by clots (ischemic stroke). The population of AF patients is around 1.5 million in the UK alone.

However, early detection allows the commencement of treatment which can allow patients to lead a normal life, and thus is of great importance. Yet, AF in early stages occurs sporadically and inconsistently in short episodes, termed "paroxysmal AF", which may be difficult to detect in short tests. This is before developing into more sustained episodes, termed "persistent AF". In these early stages, round-the-clock monitoring is necessary to capture these short episodes.

Existing solutions are adequate in detecting what is known as "clinical AF", by operating on the order of minutes and diagnosing based on the fraction of time spent in AF and non-AF. This approach minimises the potential for false alarms. However, very short episodes of AF that may be "subclinical" during the paroxysmal stage may go undetected by such algorithms.

AF is the most common type of cardiac arrhythmia and is a condition of the heart whereby the atria (upper chambers of the heart) do not coordinate well to pump blood through the body. This may allow blood clots to form, which can lead to a stroke when they travel to the brain.

Having AF increases the risk of stroke in patients by 5 times, and the overall risk of death in patients by twice. A stroke afflicts 100,000 people per year in England and Wales (equivalent to one person every 5 minutes), and 20% of all strokes caused by such clots (known as an ischemic stroke) result from AF. An estimated 1.5 million people in the UK have AF currently, and the NHS spends over £2.2 billion a year on treating AF and AF related illnesses. By the time adults reach 40 years of age, they have a lifetime risk of about 25% of developing AF.

If AF is detected, patients may be put on treatment and medication like blood thinners (Warfarin in particular), which can reduce the risk of stroke by up to two thirds, and the risk of death by one third without significantly increasing the risk of major bleeding. Stroke patients require a long recovery, and many suffer permanent neural damage. This has a significant impact on the workforce and economy, estimated to be around £2.4 billion per annum.

FIG. 1 illustrates a basic electrocardiograph (ECG) signal. This has several points, which are labelled as P, Q, R, S, and T. These features arise from the electrical signals that pass through the different heart muscles in a procedural manner to allow the heart to pump blood normally. The voltage and time statistics (height, width, and time intervals of the various features) are key to diagnosing abnormalities in the heart rhythm. Most significantly, the P wave is the result from activity in the atria.

FIG. 2 illustrates a series of ECG signals which may be used for the detection of AF by doctors in clinics. They are, in order of reliability:

Irregularly irregular R-R intervals
Missing P waves
Presence of fibrillatory waves in the ECG base line.

Using each indicator on its own has its setbacks but these indicators work well when used together. Irregular R-R intervals, while being the easiest to detect in most circumstances, may not indicate AF in some cases, as there are various other arrhythmia that also exhibit irregular R-R intervals.

Missing P waves are difficult to observe in cases where there are high noise levels, which can obscure the baseline of the ECG signal, or if the ECG leads are not placed in positions to efficiently pick up electrical signals from the atria. There are also other arrhythmia that exhibit delayed, or advanced, P waves, complicating the detection.

Fibrillatory waves on the ECG base line are the hardest to observe because they are irregular and vary in amplitude from coarse to fine. Thus they are easily obscured by noise and other interference such as electrical activity from muscles. Owing to this, fibrillatory waves are considered a "soft marker" for AF.

To make matters worse, AF occurs sporadically (termed "paroxysmal AF") in a patient at an early stage, before becoming continuous (termed "persistent AF") in a later stage of the patient. While in the early stage, a patient may only exhibit AF under specific physiological conditions (e.g. when under physical stress, if they consume alcohol, etc) and these sporadic episodes of AF may occur for very short periods of time, on the order of seconds. This means that for early detection, round-the-clock monitoring is needed so that there is the opportunity to capture and recognise these short episodes of AF.

Computer algorithms already exist for the detection of AF. The usual approach is to diagnose AF by a threshold of AF burden (i.e. percentage of beats which are AF in a certain time window), as seen in M. Carrara et al., "Classification of cardiac rhythm using heart rate dynamical measures: validation in MIT-BIH databases," J. of Electrocardiology, vol. 48, no. 6, pp. 943-946, November-December 2015. DOI: 10.1016/j.jelectrocard.2015.08.002, to reduce false positives and diagnosis. This works well for the diagnosis of what is termed as "clinical AF".

However, during the stage of paroxysmal AF, such episodes can be short enough that they can be passed over by such detection algorithms. These very short episodes are termed "subclinical AF". According to a recent investigation J. S. Healy et al., "Subclinical atrial fibrillation and the risk of stroke," The New England J. of Medicine, vol. 366, no. 2, pp. 120-129, 12 Jan. 2012. DOI: 10.1056/NEJMoa1105575, being diagnosed with subclinical AF places an individual at 5.5 times the risk of developing clinical AF, and 2.5 times the risk of stroke, both within a period of approximately 2.5 years. Early detection of AF can thus have significant impact, but requires acute accuracy in the algorithm, and at high resolutions.

Machine learning techniques have been used to classify ECG data, such as applicants U.S. application Ser. No. 15/686,948, filed Aug. 25, 2017, "A Method of Detecting Abnormalities in ECG Signals" the contents of which are hereby incorporated by reference, but considerable room for improvement exists.

SUMMARY OF THE INVENTION

According to a first aspect, there is provided a method of detecting abnormalities in an ECG signals, comprising:

receiving an ECG signal;
extracting at least one ECG beat from the ECG signal;
providing the at least one ECG beat to a neural network:
within the neural network:
performing at least two layers of convolution operations; and
for a beat of the ECG signal, determining a confidence map for the location of each of the P, Q, R, S and T points;
determining, from the respective confidence maps the position or absence of points, the points comprising each of the P, Q, R, S and T points; and
reporting the positions and/or absence of the points.

The method further may comprise:
determining a confidence map of the location of each of:
the start of the PR interval;
the start of the PR segment;
the start of the ST segment;
the end of the ST segment; and
the end of the QT interval; and
determining, from the respective confidence maps, the position or absence of further points, comprising: the start of the PR interval, the start of the PR segment, the start of the ST segment, the end of the ST segment, the end of the QT interval.

Each confidence map may have a sample rate of at least 50 Hz.

Determining a position from the confidence map may comprise applying a non-maximum suppression method to determine a position of maximum confidence for the position of the respective point.

Determining the absence of a point may comprise determining that the values of the confidence map for that point does not exceed a predetermined threshold.

The predetermined threshold may be determined by training the neural network.

The method comprises performing at least three, or at least four layers of convolution operations.

According to a second aspect, there is provided a method of producing a system for detecting abnormalities in ECG signals, comprising;
providing a neural network configured to:
perform at least two layers of convolution operations;
determine a confidence map for the location of each of a plurality of points;
determine, from the respective confidence map, a position of each of the plurality of points,
providing synthetic training data for the neural network by:
extracting a plurality of single ECG beats from ECG data;
clustering the beats based on their similarity;
sampling the beats uniformly across the clusters;
labelling the sampled beats to provide a set of labelled beats;
producing an expanded the set of labelled beats by synthetically modifying the set of labelled beats;
training the neural network using the expanded set of labelled beats, based on an error between the output of the neural network and the position of the labels in the expanded set of labelled beats.

Clustering may comprise using a k-means algorithm.

Synthetically modifying the set of labelled beats may comprise adding noise.

Adding noise may comprise adding synthetic Gaussian noise.

Synthetically modifying the set of labelled beats may comprise changing the duration of the beat.

According to a third aspect, there is provided a system for improving cardiovascular health, comprising:
a computer comprising:
a data reception module for receiving ECG data obtained from a test subject;
a beat extraction module, for extracting at least one ECG beat from the ECG data;
a neural network for determining the position or absence of each of the P, Q, R, S and T points in each ECG beat, wherein the neural network comprises:
at least two convolution layers;
a layer for determining a confidence map for the location of each of the P, Q, R, S and T points;
a layer for determining, from the confidence map, the position or absence of each of the P, Q, R, S, T points in each ECG beat; and
a reporting module for reporting the position and/or absence of the points to a patient and/or cardiologist.

The system may further comprise a beat classification module for classifying whether atrial fibrillation is present in each beat based on the position and/or absence of the points.

The reporting module may be configured to report the classification from the beat classification module to a patient and/or cardiologist.

The computer may be a server, and the data reception module may receive the ECG data via a network.

The computer may be a mobile device, and the data reception module may comprise a wireless receiver.

The reporting module may be accessible using a web based interface, and may be configured to highlight beats of an ECG in which points are absent (or in which atrial fibrillation is identified).

The system may further comprise a wearable ECG device for obtaining the ECG signals from the subject.

The system may further comprise a mobile device configured to wirelessly receive the ECG signals from the wearable ECG device, and to transmit the ECG signals to the computer.

Each of the features of each aspect (including optional features) may be combined with those of any other aspect.

BRIEF DESCRIPTION OF THE DRAWINGS

Embodiments of the invention will be described, purely by way of example, with reference to the accompanying drawings, in which.

DETAILED DESCRIPTION OF THE PREFERRED EMBODIMENTS

Figure 3:
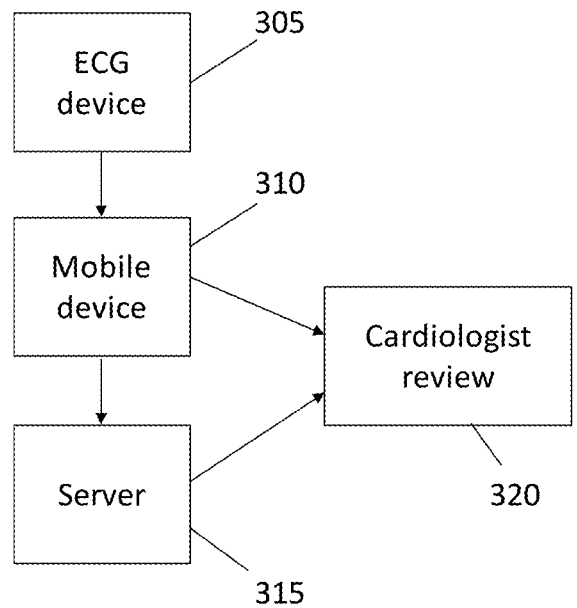
FIG. 3 is an exemplary overall architecture according to an embodiment.

FIG. 3 illustrates an exemplary overall system architecture according to one embodiment of the present invention. An ECG device 305 is provided, which comprises at least one electrode and an associated readout circuit for obtaining electrocardiogram signals from the subject. The ECG device may further comprise an analogue to digital converter for converting the ECG signal and performing any necessary processing to produce an ECG data. A microprocessor or microcontroller may be provided, configured to perform some processing on the electrocardiogram data (e.g. normalisation, filtering etc). The ECG device may further comprise a transmitter for wirelessly communicating raw or processed ECG data, for example over a low energy Bluetooth channel, or any other wireless communication channel.

The ECG device 305 may be wearable and may comprise a chest strap for holding the at least one electrode in contact with the subject in spaced apart configuration. The ECG device 305 may comprise a single electrode, or multiple electrodes.

The mobile device 310 is configured to receive the ECG data from the ECG device 305 via a data reception module (e.g. a wireless communication module). The mobile device 310 may be configured to buffer and upload the ECG data to the server 315 and/or may be configured to perform some analysis of the ECG. In some embodiments, the mobile device 310 may be configured to check for emergencies like cardiac arrest. The mobile device 310 may be responsive to the analysis, for example to send an alert or message to the cardiologist in the case of a significant abnormality. The mobile device 310 comprises a transmitter to communicate data to the server (e.g. via a mobile data communication network, such as 3G, 4G etc).

In some embodiments, the mobile device 310 is configured to perform a pre-analysis, and the server 315 is configured to run a more developed analysis on the ECG data. In some embodiments, the mobile device 310 may be configured to perform a full analysis of the ECG data locally using a neural network, and may comprise a reporting module for transmitting a report including the analysis to the server, or to a user (e.g. via a display of the mobile device). The server comprises a data reception module for receiving data via a network and a reporting module for reporting the final classification estimate to the subject and/or cardiologist. The neural network (whether it is implemented on the mobile device or the server) may provide a preliminary classification of the ECG data. The reporting module may provide a report in which regions of interest in the ECG data are highlighted to facilitate straightforward review by the cardiologist 320. This may greatly reduce the workload on the cardiologist 320, and render feasible monitoring of subject ECGs over long periods (e.g. continuously or nearly so).

Figure 4:
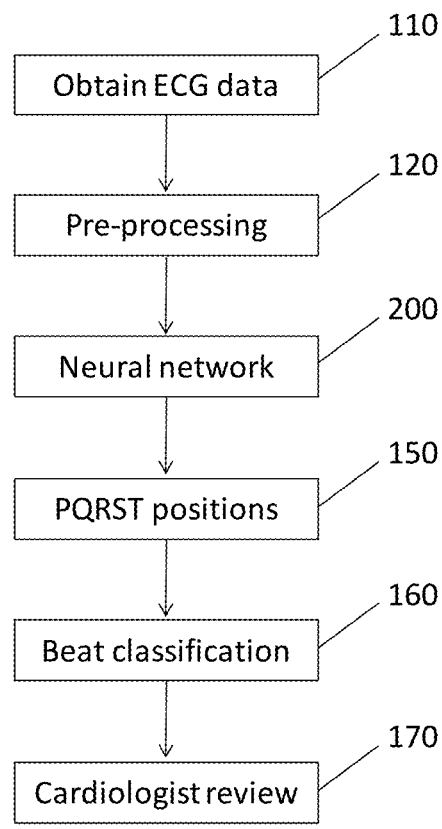
FIG. 4 is an overall methodology for detecting abnormalities in ECG signals according to one embodiment.

Referring to FIG. 4, an overview of a process for identifying abnormalities in ECG data is shown.

At 110 ECG data is obtained, for example using the ECG device 305 described with reference to FIG. 3, or from either the mobile device 310 or the server 315.

At 120 the ECG data is pre-processed. The pre-processing step may comprise identifying each beat of the ECG data, for instance using a Pan and Tompkins QRS complex detector, [see Pan, Jiapu and Tompkins, Willis J. A real-time QRS detection algorithm. IEEE transactions on biomedical engineering, (3):230-236, 1985], or any other method (e.g. RR detection, based on filtering and identification of local maxima, etc).

The step of pre-processing 120 may further comprise at least one of filtering, normalising and re-sampling the identified beat to a specific data rate. In an embodiment, the pre-processing step may comprise re-sampling ECG beat. The re-sampling may be to a fixed number of samples in the beat.

At 200 a neural network is used to locate the PQRST points in each beat of the ECG data. In addition, other significant locations for each beat may be determined, for example, including: the start of the PR interval, the start of the PR segment; the start of the ST segment; the end of the ST segment; and the end of the QT interval. The neural network 200 may be configured to determine the positions of each location on the ECG beat using a confidence map that indicates a confidence that each location in the beat may be the location of the point in question. For example, a point of maximum confidence may be assumed to be the location of the point.

The neural network may be a convolutional neural network (CNN).

At 160 the location of each of the points identified by the neural network may be used to classify each beat of the ECG as normal or abnormal, or more specifically, as "AF" or "non-AF". The morphology of the PQRST waves and their relationships to each other describe the wave in a low dimensional form useful for determining various types of abnormalities. Cardiologists presently manually locate these attributes when forming a diagnosis. As an example, one such abnormality is the absence of a P-wave which would indicate AF. In some embodiments, the system may not automatically classify an ECG beat, but may instead be configured to pass on useful attributes (e.g. the location of the points and/or the absence of any of the points) of the ECG beat to a different external system for classification (which could be another neural network, or a cardiologist). In this way the way the classifier forms its decision becomes more transparent, and we gain better human interpretability as to why such a diagnosis is made. In comparison, it is very difficult to interpret why a certain diagnosis is made in a "black box" system which uses the raw signal as an input and merely provides a classification (it is notoriously difficult to reverse engineer how and why a trained CNN functions, for example).

The classification output from the beat classification step may comprise a probability corresponding with each of a plurality of classifications for each ECG beat of the input ECG signal. For example, the beat classification step may use classifications of "AF" and "not-AF", and the beat classification may provide an estimate of the probability for each beat of the ECG data being "AF" and "not-AF". Since these example classifications are mutually exclusive, the sum of their probabilities may be equal to 1, but it will be appreciated that this will not necessarily be the case (depending on what classifications are sought from the neural network). Other classification types may be used.

In some embodiments the neural network and/or the beat classification step may be implemented on a server (e.g. in the cloud, and/or remote from the user), for example by providing using GPU processing, or on a specialised neural processing unit (e.g. Intel Nervana, Google Tensor processing unit, Apple Neural Engine, Cadence Tensilica or similar). The neural network may be hosted by a cloud computing service such as Amazon Machine Learning services, Azure Machine Learning, Google Cloud AI or similar.

A server based neural network (or cloud service) may be able to rapidly and efficiently process data from a large amount of different users, and provide a platform that can be accessed by a cardiologist to review the information. In other embodiments the neural network may be implemented locally (for example on a mobile device). This may mean that patient identifiable data is be kept local to the patient's own device.

The results may be made available for review by a cardiologist, for example via a web accessible platform. The platform may provide ECG data to the cardiologist with regions of particular interest highlighted, based on the beat classification 160. For example, beats or regions classified as "AF" with a probability of greater than a predetermined threshold (e.g. 0.8) may be flagged or highlighted for further review by a cardiologist. A duration based threshold may also be used in determining regions of interest (e.g. AF with a probability of >0.8, over a time period of at least 2 ECG beats).

Figure 5:
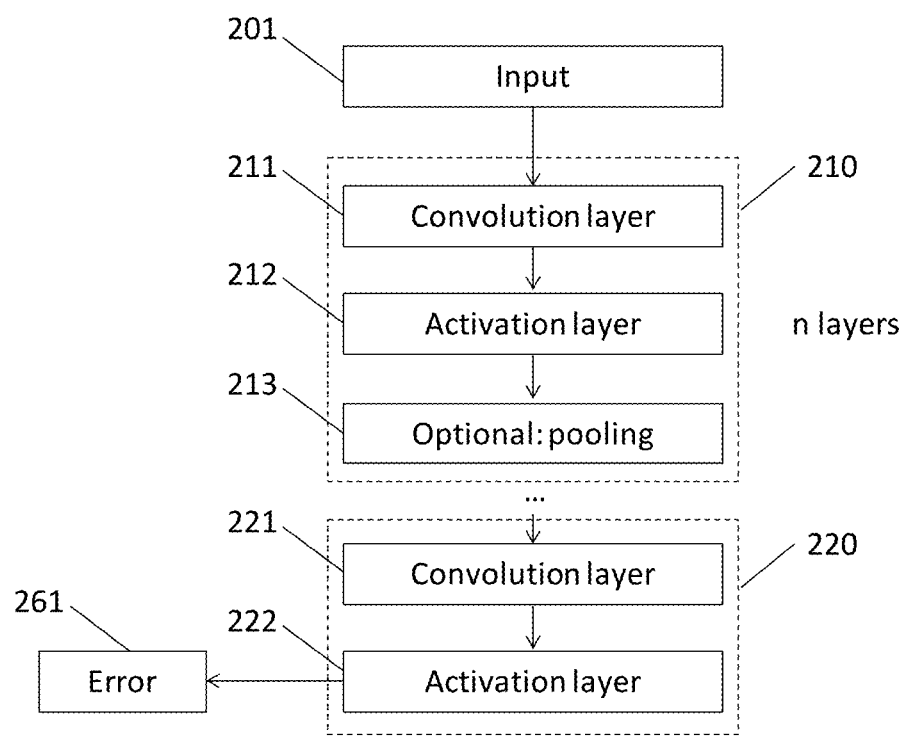
FIG. 5 is a schematic diagram of a neural network for use in an embodiment.

FIG. 5 illustrates an example neural network in schematic form for locating PQRST points in ECG beats. The neural network comprises an input layer 201 followed by n superlayers 210 and a confidence map superlayer 220. Each superlayer 210 comprises a convolution layer 211, activation layer 212 and optionally may include a pooling layer 213. In some embodiments, the pooling layer may be omitted in one or all of the superlayers.

Each convolution layer 211 applies one or more convolution filters (or kernels) by stepping the filter over the data provided to that layer (the steps having a predetermined stride distance). The output from each convolution layer 211 comprises the data produced from the convolution of the input data with each filter.

Subsequent to the convolution layer 211, an activation layer 212 is provided, which maps the output of the convolution layer 211 to a different range of values. Typically, the activation function used in each of layers 210 will be a rectified linear activation function (ReLU), but other activation functions may also be used.

Where pooling layers are used (and these are not essential), these may reduce the spatial dimension of the data before the next layer. The pooling function used may (for instance) be a max pooling with a stride greater than 1, but other pooling approaches may also be used. The output from the pooling layer is provided to the subsequent superlayer 210 (if it is present). If no pooling layer is used, the output from the activation function (e.g. ReLU) may be provided directly to the next convolution layer.

The sequence of n superlayers 210 are followed by the confidence map superlayer 220, which comprises a convolution layer 221 and an activation layer 222. The output from layer 222 is a confidence map for each point to be located (e.g. PQRST), comprising a set of confidence levels that each of a plurality of times in the input ECG signal corresponds with the particular position (e.g. a matrix with a row of confidence vectors for each point to be located). An estimate for the location of each point can be determined from the confidence map, for example by finding the position of a maximum confidence (e.g. by non-maximum suppression). If the position of maximum confidence has a confidence level that is below a threshold, the point can be considered to be absent. The threshold for a point to be considered absent may be determined during training of the network (i.e. an optimum value that maximises agreement with cardiologists).

An error 261 can be determined from the confidence maps based on a true position of each point for its respective confidence map. This error 261 may be used as part of a penalty function in training the network. The error 261 may be determined in the form of a cross entropy loss.

Figure 6:
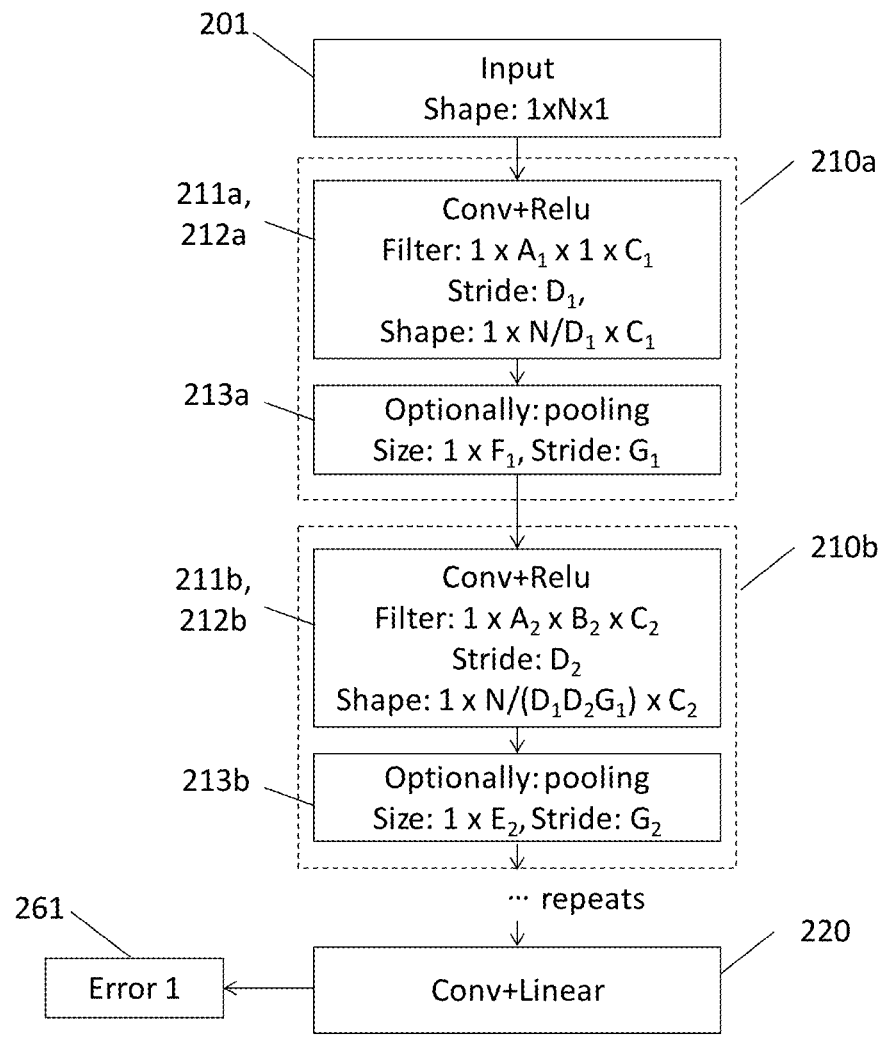
FIG. 6 is a further schematic diagram of a neural network for use in an embodiment.

FIG. 6 illustrates an example architecture for the layers in more detail. The input layer 201 comprises an input vector of ECG data, with dimension 1×N×1, with the second dimension N being the number of samples (i.e. corresponding with time). In some embodiments the (first) dimension of the input data may be higher, for example in the case of input data comprising having multiple channels (e.g. each corresponding with raw data obtained from each of a plurality of electrodes).

The input data is provided to first superlayer 210a, which comprises a convolution layer (cony) 211a, and ReLU layer 212a. The first cony layer 210a may apply $C_1$ filters, each having a kernel of dimension $1 \times A_1 \times 1$, with a dilation factor $E_1$ and a stride of $D_1$. The shape of the output from the cony and ReLU 211a, 212a is of dimension $1 \times N/D_1 \times C_1$ (the length of the vector is decreased in proportion to the stride, and the third dimension (which can be thought as as rows) increased in proportion to the number of filters applied by the cony layer 211a, since there is an output vector per filter). The number of filters $C_1$ in the first cony layer 210a may be at least 8, and may be in the range 8 to 64, for example 16 or 32. The stride of the cony 211a may be 1, so that the neural network can discriminate features with maximum resolution. The kernel dimension $A_1$ may be in the range 2 to 32, for example 15 or 16.

The subsequent optional pooling layer has a size $1 \times F_1$ and a stride $G_1 > 1$, so that the second spatial dimension following the pooling is reduced by a factor of $G_1$. The next superlayer 210b therefore receives data with extent $1 \times N/(D_1 G_1) \times C_1$.

The second superlayer 210b comprises $C_2$ filters, each with extent $1 \times A_2 \times B_2$. Preferably, $B_2 = C_1$ (or more generally for $i \geq 2$, $B_i = C_{i-1}$), so that each cony filter is stepped over all the data from the previous layer in only one direction. The number of filters $C_2$ in the second superlayer 210b is preferably in the range 16 to 128, for example 32. The output from the second cony and ReLU 211b, 212b is of dimension $1 \times N/(D_1 D_2 G_1) \times C_2$. The stride of the second cony layer 211b (and successive layers) is preferably 1, for the same reasons as for the first layer, but this is not essential (for example, a higher stride may be appropriate for ECG data with high sampling frequency).

The temporal resolution of the output of each successive layer is reduced by the product of the stride distances of the preceding layers and may successively decrease. In some embodiments a stride of 1 is used in each cony layer without pooling, which results in no loss of temporal resolution through the successive layers.

The confidence map is produced using a filter for each point (e.g. each of PQRST), followed by a linear activation layer, which maps the output of each filter onto a set of confidence levels that a particular time corresponds with one of the points of interest.

Estimates for the positions of the points of interest can be obtained by selecting a maximum value from each of the confidence maps (e.g. using a non-maximum suppression method). The absence of a particular point of interest may be identified by the confidence map not exceeding a threshold value, or the value of confidence obtained by non-maximum suppression not exceeding the threshold value. The threshold value may be determined by training of the neural network, as the value that minimises a penalty function (i.e. so as to maximise the probability of agreement with a cardiologist).

Figure 1:
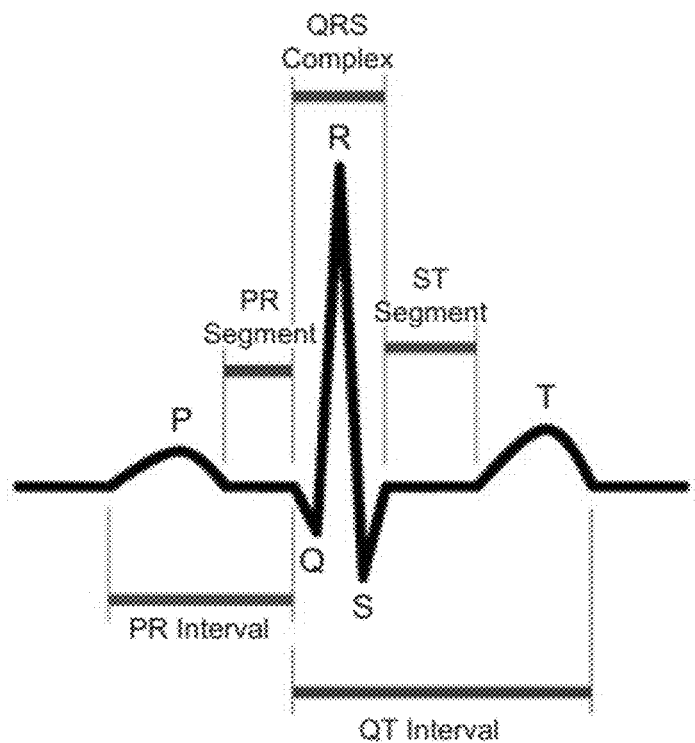
FIG. 1 is a graph of a basic electrocardiograph (ECG) signal.
Figure 2:
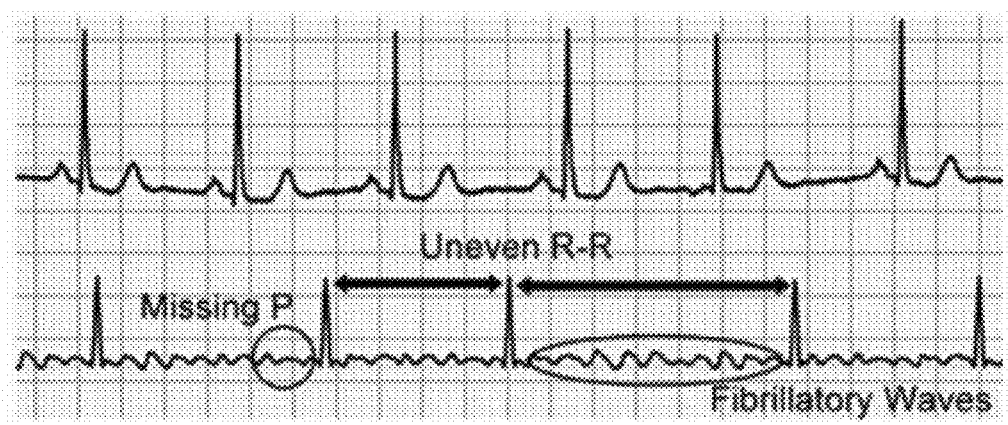
FIG. 2 is a series of ECG signals which may be used for the detection of AF by doctors in clinics.

A neural network following the architecture described in FIGS. 5 and 6 was implemented, capable of receiving a beat of ECG data and identifying the PQRST points and other points of interest (as discussed above with reference to FIG. 1).

The neural network was trained using single beats extracted from ECG recordings downloaded from physionet. Beats were detected using the Pan and Tomkins QRS complex detector. Each beat was linearly resampled to cover 256 sample points. Training labels (i.e. the locations of each of the points of interest) were provided by human experts.

In order to efficiently generate sufficient training data, an algorithm was developed to produce a large number of labelled training beats from a smaller volume of labelled beats. All beats from a collection of ECG data (e.g. on the order of $10^5$ beats) were clustered using a k-means algorithm, Each cluster represents a beat with slightly different attributes to the neighbouring clusters. A sample of diverse ECG beat types was obtained for manual scoring by sampling uniformly across clusters.

A skilled human expert manually labelled the beats sampled from each cluster. This labelled training data was manually expanded by synthetically augmenting the data. The data was synthetically augmented in a number of ways, including adding synthetic noise (e.g. Gaussian noise), and by changing the duration of the ECG beat (e.g. by a linear transformation). This maximises training performance with a minimal amount of training effort.

Figure 7:
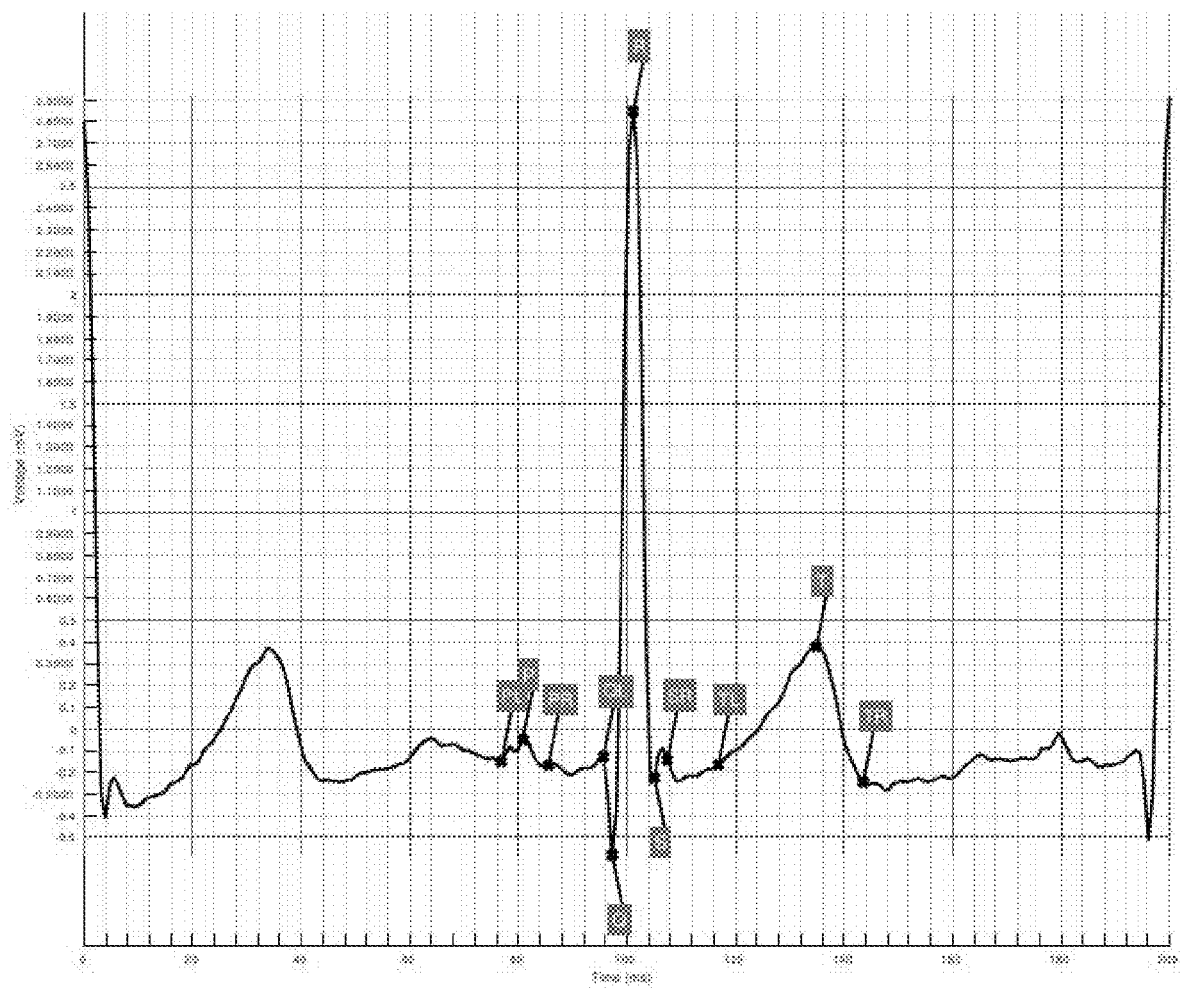
FIG. 7 is an example "normal" ECG beat in which the locations of points have been identified in accordance with an embodiment.

FIG. 7 illustrates an extracted beat of an ECG (i.e. a region starting with an R point of a previous beat, including an R point of the extracted beat, and ending with an R point of a subsequent beat. Each of 11 points have been located by a neural network according to an embodiment, these being:

P, Q, R, S, T points (labelled as such),
the start of the PR interval (labelled PL),
the start of the PR segment (labelled PR),
the end of the PR segment/start of the QRS complex/start of the QT interval (labelled QL),
the start of the ST segment/end of the QRS complex (labelled SR),
the end of the ST segment (labelled TL),
the end of the QT interval (labelled TR).

In this beat each of the normal points are present, and have been located. The locations of the points of this beat have been classified as normal.

Figure 8:
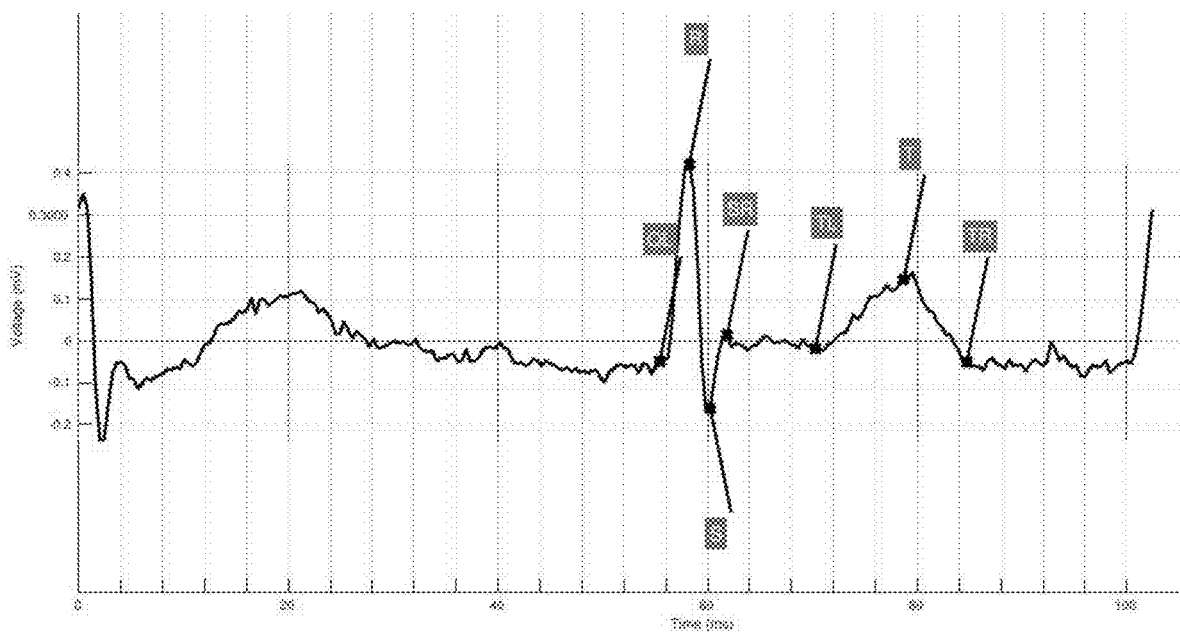
FIG. 8 is an example AF ECG beat in which the absence of a P wave has been identified in accordance with an embodiment, and the location of other points has been identified.

FIG. 8 shows an extracted beat of an ECG in which the P wave is missing. Each of the PL, P and PR points have therefore not been located on the ECG, because these points are based on the location of the P wave.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

Although a number of examples have been described, these are not intended to limit the scope of the invention, which is to be determined with reference to the accompanying claims.

The invention claimed is:

1. A method of producing a system for detecting abnormalities in electrocardiogram (ECG) signals, comprising;
   providing a neural network configured to:
      perform at least two layers of convolution operations;
      determine a confidence map for a location of each of a plurality of points;
      determine, from the respective confidence map, a position of each of the plurality of points, the points corresponding with one or more of a P, Q, R, S and T feature in each beat of the ECG signal,
   providing synthetic training data for the neural network by:
      extracting a plurality of single ECG beats from ECG data;
      clustering the beats based on their similarity;
      sampling the beats uniformly across the clusters;
      labelling the sampled beats to provide a set of labelled beats; each labelled beat comprising a position of one or more of a P, Q, R, S, and T features;
      producing an expanded set of labelled beats by synthetically modifying the set of labelled beats;
   training the neural network using the expanded set of labelled beats, based on an error between an output of the neural network and the positions of the labels in the expanded set of labelled beats.

2. The method of claim 1, wherein clustering comprises using a k-means algorithm.

3. The method of claim 1, wherein synthetically modifying the set of labelled beats comprises adding noise.

4. The method of claim 3, wherein adding noise comprises adding synthetic Gaussian noise.

5. The method of claim 1, wherein synthetically modifying the set of labelled beats comprises changing the duration of the beat.

\* \* \* \* \*